United States Patent [19]

Borsotti et al.

[11] Patent Number: 5,432,268
[45] Date of Patent: Jul. 11, 1995

[54] PROCESS FOR PRODUCING HYDROXYALKYL GLUCOSIDES

[75] Inventors: Giampietro Borsotti, Novara; Massimo Ciali, Milan; Tullio Pellizzon, Paderno Dugnano; Giovanni Agnes, Novara, all of Italy

[73] Assignees: Enichem S.p.A.; Eniricerche S.p.A., both of Milan, Italy

[21] Appl. No.: 59,121

[22] Filed: May 7, 1993

[30] Foreign Application Priority Data

May 15, 1992 [IT] Italy .................. MI92A01156 U

[51] Int. Cl.6 .................. C07H 15/00; C07H 15/04
[52] U.S. Cl. .................. 536/18.5; 536/4.1; 536/18.6; 536/120; 536/124
[58] Field of Search .................. 536/18.5, 18.6, 120, 536/124, 4.1

[56] References Cited

U.S. PATENT DOCUMENTS

| H619 | 4/1989 | McDaniel et al. | 536/18.6 |
|---|---|---|---|
| 2,374,236 | 4/1945 | Salzberg et al. | 260/210 |
| 2,407,001 | 9/1946 | Griffin | 260/209 |
| 2,407,002 | 9/1946 | Griffin | 260/210 |
| 2,407,003 | 9/1946 | Griffin | 260/210 |
| 3,565,885 | 2/1971 | Molotsky et al. | 260/210 |
| 3,585,185 | 6/1971 | Levis et al. | 260/210 |
| 3,758,410 | 9/1973 | Liu | 252/89 |
| 3,839,318 | 10/1974 | Mansfield | 260/210 |
| 4,301,089 | 11/1981 | Pesa et al. | 260/465.1 |
| 4,595,671 | 6/1986 | Venturello et al. | 502/159 |
| 4,612,301 | 9/1986 | Currie et al. | 502/154 |
| 4,866,165 | 9/1989 | Lüders | 536/18.6 |
| 4,898,934 | 2/1990 | Lueders et al. | 536/18.6 |
| 4,950,743 | 8/1990 | McCurry et al. | 536/18.6 |
| 4,990,605 | 2/1991 | Lueders | 536/18.5 |
| 5,003,057 | 3/1991 | McCurry et al. | 536/18.6 |
| 5,166,337 | 11/1992 | Ripke | 536/126 |
| 5,212,292 | 5/1993 | Ripke | 536/18.6 |

FOREIGN PATENT DOCUMENTS

| 0112679 | 4/1984 | European Pat. Off. |
| 0402978 | 12/1990 | European Pat. Off. |
| 1501916 | 11/1967 | France |

OTHER PUBLICATIONS

E. S. Gould: "Mechanism and Structure in Organic Chemistry" 1st Edition, pp. 98–99, Holt, Rinehart and Winston, N.Y.

D. S. Kemp, et al. "Organic Chemistry", 1st Edition, pp. 373–375, Worth Publishers, Inc., N.Y.

*Primary Examiner*—Douglas W. Robinson
*Assistant Examiner*—Howard C. Lee
*Attorney, Agent, or Firm*—Rogers & Wells

[57] ABSTRACT

A process is disclosed for producing particular hydroxyalkyl glucosides in the presence of a binary catalyst.

13 Claims, No Drawings

PROCESS FOR PRODUCING HYDROXYALKYL GLUCOSIDES

The present invention relates to a process for producing particular hydroxyalkyl glucosides.

The field of surfactants has seen a considerable development during the past years; a large share of the world market is constituted by non-ionic surfactants, and in particular, by polyethoxylated alcohols and polyethoxylated alkyl-phenols.

Such non-ionic surfactants have gained a considerable importance thanks to their good detergent properties, to the flexibility in the various formulations (compatibility with ionic surfactants) and to their low production cost.

Besides these classes of non-ionic surfactants, new classes have been developed recently, which are characterized by hydrophilic moieties different from polyethoxy groups; among these, the esters of mono- and oligosaccharides seem to be particularly attractive, owing to their low cost and intrinsic biodegradability.

However, these types of long chain esters, derived, e.g., from palmitic acid, are not satisfactory from the practical viewpoint, owing to the limited stability of the ester group at pH values higher than 8, necessary in a large number of formulations.

Such a limited chemical stability was overcome by introducing ether bonds resulting from the reaction of epoxides with a hydroxyethyl glucoside, as disclosed in Italian Patent Application No. MI-91A-001427, to the name of Enichem Augusta S.p.A.

The Applicants have made further steps ahead in an attempt of simplifying the process, simultaneously obtaining better yields.

Therefore, the subject matter of the present invention is a process for producing hydroxyalkyl glucosides of general formula (I):

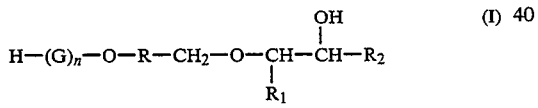

(I)

wherein:
R may be a moiety selected from $-CH_2-$ or $-CH_2-CH_2-$ or $-CH_2-CHOH-$;
$R_1$ and $R_2$ may be alkyl radicals, each of them with 1-18 carbon atoms;
$R_1$ or $R_2$ may also be hydrogen atoms, but never simultaneously;
the total number of carbon atoms of $R_1$ and $R_2$ shall not be higher than 18;
G is a radical resulting from the removal of a molecule of $H_2O$ from a monosaccharide, commonly designated as a "reducing sugar", typically a hexose or a pentose of formula $C_6H_{12}O_6$ or $C_5H_{10}O_5$;
n is an integer comprised within the range from 1 to 5;
said process comprising:
(a) reacting an epoxide of an olefin, of from 8 to 20 carbon atoms, with a diol or a triol in the presence of a catalyst, with the glycol-ether (II) being obtained;
(b) performing a reaction of glycosidation of the glycol ether (II) with a reducing sugar or a compound which can supply a reducing sugar by hydrolysis, or with a methyl-, ethyl- or butyl-glucoside derived from said reducing sugar; characterized in that the reaction of step (b) is carried out in the presence of a binary catalyst constituted by a strong organic acid and a weak organic base having a Ka value within the range of from $10^{-8}$ to $10^{-1}$.

As regards the reducing sugar, types of hexoses or pentoses which may be used are: glucose, mannose, galactose, arabinose, xylose, ribose and the like.

Also the higher sugars or substituted saccharides can be used, which can be hydrolyzed in order to yield monosaccharides: among these starch, maltose, saccharose, lactose, maltotriose, methyl-, ethyl- or butyl-glucosides, and so forth.

Owing to its low cost and its large availability, glucose is the preferred monosaccharide.

In order to better exemplify the process according to the present invention without limiting it, the following reaction scheme is proposed:

Step (a):

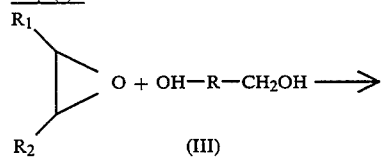

(III)

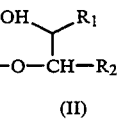

(II)

Step (b):

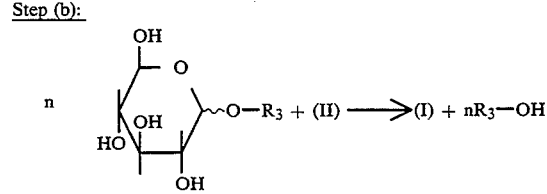

in which R, $R_1$ and $R_2$ have the same meaning as defined above and $R_3$ is H, $CH_3$, ethyl, butyl.

The preparation of (II) [Step (a)] is known; for example, in U.S. Pat. No. 3,758,410, the reaction was disclosed of an epoxide with ethylene glycols in the presence of acidic catalysts.

The opening of the epoxidic ring can also be accomplished by means of a basic catalysis, for example, when, in the case of alpha-epoxides, exclusively the product deriving from nucleophilic attack to the terminal carbon atom has to be formed, according to the paper by P. E. Parker and N. S. Isaac, Chem Rev., 1959, 59, 737.

In considering, on the contrary, Step (b), problems arise as regards the reaction of glycosidation because, usually, undesired reactions take place.

For example, U.S. Pat. No. 4,950,743 reports that one of such undesired reactions is the formation of polyglucose or of polyhydroxymethyl furfural.

The first by-product, if present in the end product, leads to an excessive foaming of surfactant solutions, and the second one is responsible for the appearance of an undesired yellow-brown colours.

The formation of polyglucose, as regards the economy of the reaction, also means a loss of yield of desired product.

A large number of patents aim at achieving the specific target of preventing polyglucose formation; for example, in WO Patent No. 90/07516, the use of a high-lipophilicity catalyst suitable for overcoming this problem is disclosed.

However, also in this case, although it is decreased relatively to the use of traditional acids, the formation of polyglucose is not completely prevented.

Therefore, the primary purpose of the present invention is obtaining a glycosidation product which is free from such by-products as polyglucose, and in this regard the present Applicants have found that the catalytic system used in Step (b) makes it possible for the drawbacks of the prior art, described above, to be overcome.

The reaction of glycosidation [Step (b)] is hence carried out in the presence of a binary catalyst consisting of a strong organic acid and a weak organic base, with a Ka value within the range of from $10^{-8}$ to $10^{-1}$.

Examples of strong organic acids are: benzene- or alkylbenzene sulfonic acids, naphthalene or alkylnaphthalene sulfonic acids, primary, secondary or tertiary alkyl sulfonic acids, monoalkylsulfates, mono- and dialkylphosphates, alkyl-, aryl- or alkylaryldisulfonic acids, in which all of the aliphatic chains contain from 1 to 20 carbon atoms, and sulfonic groups containing cation exchange resins.

Example of weak organic bases are pyridine, picolines, lutidines, collidines, quinoline, isoquinoline, quinaldine, pyrazine, pteridine, tetramethylurea, and so forth.

The catalyst can be easily prepared separately or in situ by blending equivalent amounts of said acids and bases.

Preferred catalysts are the salts of pyridine with alkylbenzene sulfonic acids or secondary alkyl sulfonic acids, with the latter being obtainable for example, according to Italian Patent Application No. 20878 A/89 to the name of Enichem Augusta S.p.A., the content of which is therefore incorporated herein by reference.

Among all, preferred is the salt of pyridine with secondary alkyl sulfonic acids (SASA) containing from 14 to 17 carbon atoms.

The catalyst can be used in amounts within the range of from 0.001 to 0.1 mol per mol of reducing sugar, or of an equivalent thereof as defined hereinabove, and preferably of from 0.001 to 0.05 mol.

The unique character of this catalyst is demonstrated by a comparison test as disclosed in Example 8, in which the glycosidation reaction is carried out in the presence of such conventional acid as p-toluene sulfonic acid.

By operating under the same conditions of temperature, pressure, and rate of stirring of the reaction mass as of the test of Example 7, and quenching both said reactions when the stoichiometric amount of water is distilled off, in Example 8 a considerable amount of polyglucose was formed, whilst, on the contrary, when the catalyst of Example 7 was used, glucose was prevailingly present which could consequently be recovered and used again.

The end product is hence completely free from polyglucose, that constitutes a typical feature of the present process as compared to the prior art.

When such catalysts as disclosed above are used, the kinetic control of the reaction is easier because, for example, products of formula (I) with a high level of hydroxyalkyl-monoglucosides [e.g., mixtures containing more than 70% of product with $n=1$ in formula (I)] are obtained more easily.

Furthermore, by using said binary catalysts, at the end of the reaction lighter-coloured products are obtained than the corresponding products obtained with conventional acidic catalysts such as, e.g. p-toluene sulfonic acid.

However, if, in order to remove the excess of glycol-ether (II) a distillation is used, which requires a temperature of the order of 190°–200 °C. and residual pressures within the range of from 0.2 to 0.5 mmHg, brown coloured products are obtained, in particular if the distillation time exceeds 1–2 hours.

However, the latter does not constitute a problem because the aqueous solutions of the surfactant can easily be adjusted at a more than acceptable colour by using any of the large number of reactants known from scientific literature, such as $H_2O_2$ used in U.S. Pat. No. 3,450,690, sodium perborate disclosed in U.S. Pat. No. 3,839,318, or other equivalent bleaches, such as alkaline hypochlorites, persulfates, and so forth.

In Step (a) of the process according to the present invention, the diol is used in an amount which may be the same as, or larger than, the stoichiometric amount of epoxide (III), and namely, of from 1 to 15 mols per mol of epoxide (III), whilst in Step (b) the glycol-ether (II) is used in an amount which is the same as, or larger than, the stoichiometric amount of the reducing sugar, as better defined in the following.

Furthermore, in Step (a) of the process the diol also acts as a solvent, i.e. as the liquid media for the reaction mixture; in Step (b) the solvent function is performed by the glycol-ether (II).

As the reactant in Step (a), mixtures of epoxides having the general formula (III) are generally used in which $R_1$ and $R_2$ have the same meanings as specified hereinabove; these mixtures are obtained in turn by reacting corresponding mixtures of linear olefins with hydrogen peroxide, according to such methods as disclosed, for example, in GB Patent No. 2,055,821 and in U.S. Pat. No. 4,595,671.

In the reaction of glycosidation [Step (b)] the molar ratio of the reducing sugar, or its equivalent as already defined above, to the glycol-ether (II) is comprised within the range of from 1:2 to 1:10 and preferably of from 1:3 to 1:6.

The selection of the value of such molar ratio makes it possible for the characteristics of the end product of formula (I) to be controlled; so, if a product is desired which has a high polymerization degree (n), such low ratios as 1:2 will be used; whilst, if a product prevailingly containing hydroxyalkyl-monoglucoside ($n=1$) is desired, high values of such a ratio as 1:6 will be used.

The reaction temperature is comprised within the range of from 90° to 130° C.; a preferred range is from 110° to 120° C.

During the condensation of Step (b), $R_3$—OH (in which $R_3$ has the already specified value) is formed, which can be removed with a stream of an inert gas, such as nitrogen, or by distillation if the reaction is carried out under a reduced pressure.

In order to obtain large amounts of hydroxyalkyl-monoglucosides [formula (I) with $n=1$] the reaction is suitably discontinued when the conversion of carbohydrate is still incomplete.

In that case, in order to more easily recover the unreacted carbohydrate, the reaction mass is suitably diluted with a solvent in which said carbohydrate is insoluble, such as hexane or heptane.

Such a dilution results also in the advantage that the reaction mixture is made more fluid, therefore more easily separable by carbohydrate filtering.

The use of said diluents also causes the partial precipitation of the catalyst which consequently can be (partially) recycled.

The filtrate solution is admixed with at least 1 mol of a strong base per each mol of catalyst used.

By "strong bases" the alkali metal or alkaline-earth metal hydroxides and alkali-metal alkoxides are meant.

Preferred bases are sodium hydroxide and sodium methoxide.

From the resulting mixture the dilution solvent is recovered under a low vacuum (30–150 mmHg), in the rotary evaporator, and with the kettle temperature being comprised within the range of from 30° to 100° C.

Then the unreacted glycol-ether of formula (II) is distilled off under a residual pressure of 0.1–0.5 mmHg with a kettle temperature of 190°–200° C.

Such a distillation can be carried out by means of a traditional apparatus or, preferably, with a thin film evaporator.

The residue resulting from said distillation is subsequently dissolved in water (e.g., using a same water volume as of said residue, in order to obtain a solution at 50% by weight/weight) and is decolourized according to known methods, as described hereinabove.

Lipophilic components still present in the aqueous solution [and generally constituted by the reactant of formula (II) not completely removed during the distillation step and/or by products of degradation thereof] are suitably removed by solvent extraction.

Suitable solvents for such a purpose are ethylether and ethyl or propyl acetate.

Preferred solvent is ethyl acetate.

The following Examples are supplied for merely illustrative purpose and in no way should be construed as being limitative of the present invention.

EXAMPLE 1

Opening of the internal $C_{11-12}$ epoxide with ethylene glycol

A mixture 900 g of internal $C_{11-12}$ epoxide (with an epoxide content of 95%) with 3000 g of ethylene glycol is heated at 80° C.

1.25 cc of etherated $BF_3$ is added, the reaction is stirred for 1 hour and the disappearance of the epoxide is verified by thin-layer chromatography with eluent petroleum ether:ethyl ether=2:1.

The reaction mixture is alkalified with 5 g of a solution of NaOH at 50% w/w and is distilled under reduced pressure.

After recovering the excess of ethylene glycol, 1022 g of colourless product (I) with a boiling point of 135°–160 °C./0.2 mmHg is collected.

The resulting product has formula (I):

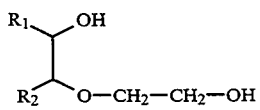

(1)

in which both of $R_1$ and $R_2$ are linear alkyl radicals and different from H and such that $R_1+R_2=9-10$ carbon atoms.

The yield based on epoxide is 91%.

EXAMPLE 2

Reaction of product (1) with glucose 100 g of glycol ether (1) and 18 g of anhydrous glucose are added to a flask of 250 cc equipped with stirrer, thermometer, distillation head and dipping tube for nitrogen injection.

The reaction mixture is heated up to 119°–120° C. under a nitrogen flow and 0.3 g of pyridinium p-toluenesulfonate (Py.p-TSA) is added.

The reaction mixture heating is continued under a nitrogen flow for 6 hours, with water being continuously removed as soon as it is formed.

When the reaction is complete, the reaction mixture is diluted with 100 cc of heptane and is filtered; the precipitate, washed with heptane and dried, has a weight of 2.75 g and is prevailingly constituted by glucose.

The filtrate solution is admixed with 65 mg of $CH_3ONa$ and the resulting mixture is distilled; recovered are firstly heptane, in Rotavapor at 20 mmHg. and at 50°–100 °C., and then 82.5 g of glycol-ether (1), at 0.1 mmHg, by heating with an oil bath at 190° C.

The distillation residue is dissolved in 50 cc of water and then is treated at 20°–30° C. with a solution of sodium hypochlorite until positive reaction with starch-iodine paper.

The solution is extracted with 100 cc of ethyl acetate and, by evaporation uder reduced pressure, the surfactant containing aqueous phase yields 28 g of a solid, glassy and slightly yellow-coloured product. According to an alternative route, the product can be concentrated at 50–60%.

An aqueous solution at 50% w/w displays an absorbance at 470 nm of 0.12 ($E_{470}=0.24$).

The product, analysed by HPLC (high-pressure liquid chromatography) and by GC (Gas chromatography), after being preliminarily silanated, results to have the following composition:

| | |
|---|---|
| hydroxyalkyl-monoglucoside = | 70–72% |
| hydroxyalkyl-diglucoside = | 16–18% |
| hydroxyalkyl-triglucoside = | 4–5% |
| hydroxyalkyl-tetraglucoside = | 1.5% |
| hydroxyalkyl-pentaglucoside = | 0.5% |
| glucose = | less than 0.1% |
| polyglucose = | none |
| glycol-ether (1) = | less than 1% |

EXAMPLE 3

Opening of the internal C11-12 epoxide with glycerol

A mixture of 410 g of glycerol with 105 g of $C_{11-12}$ epoxide (containing 95% of epoxide) is heated at 90° C.

0.5 cc of etherated $BF_3$ is added, then the reaction mixture is stirred for 1 hour.

The reaction mixture is cooled, the bottom phase essentially constituted by glycerol is separated, the upper phase is diluted with petroleum ether and is washed first with a solution at 5% of $NaHCO_3$ and then with $H_2O$, until neutral.

By evaporating the solvent, 136.5 g of raw product (2) is obtained as a thick, nearly colorless oil which can be used as such in the subsequent reaction with glucose.

According to an alternative route, the product (2) can be purified by distillation under a reduced pressure of 0.1 mmHg and at 170°–190° C.

The resulting product has the formula (2):

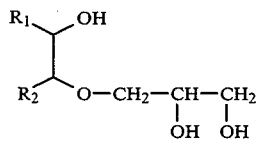

in which both of $R_1$ and $R_2$ are linear alkyl radicals and different from H and such that $R_1+R_2=9-10$ carbon atoms.

EXAMPLE 4

Reaction of product (2) with glucose 95 g of the raw triol (2), as obtained from Example 3, and 18 of anhydrous glucose are added to the same reaction equipment as of Example 2.

The reaction mixture is heated up to 119°–120° C. under a nitrogen flow and then 0.3 g of (Py.p-TSA) is added.

The reaction mixture heating is continued under an $N_2$ flow for 6 hours, with water being continuously removed as soon as is formed.

At the end, the reaction mixture is diluted with 100 cc of heptane and is filtered; the precipitate, washed with heptane and dried, has a weight of 2.4 g and is prevailingly constituted by glucose.

The filtrate solution is admixed with 65 mg of $CH_3ONa$ and the resulting mixture is distilled; recovered are firstly heptane, in Rotavapor at 20 mmHg and at 50°–100° C., and then 76 g of tryol (2), at 0.1 mmHg, by heating with an oil bath at 210° C.

The distillation residue, dissolved in 50 cc of water and then treated as in Example 2, yields, after evaporating the aqueous solution, 29 g of a solid, foam-like and slightly yellow product.

An aqueous solution at 50% w/w displays an absorbance at 470 nm of 0.175 ($E_{470}=0.35$).

EXAMPLE 5

Hydroxyalkyl-polyglucosides by transacetalation from butyl-glucoside 100 cc of n-butanol, 18 g of anhydrous glucose and 0.3 g of Py.P-TSa are charged to the apparatus of Example 2.

The reaction mixture is refluxed with a Marcusson, with water being removed as is formed, until a clear and colourless solution is obtained, which is constituted by a mixture of alpha+beta butyl-glucoside in N-butanol.

100 g of glycol-ether (1) is added and butanol is distilled off under reduced pressure, with the inner temperature of the reaction vessel being kept at 115° C.

Four hours later, the disappearance of butyl-glucoside is verified by thin-layer chromatography with eluent chloroform:methanol=3:1.

The reaction mixture is diluted with 100 cc of heptane, any insolubles are filtered off and and the resulting solution is alkalified with 65 mg of $CH_3ONa$ and then is distilled.

By operating as in Example 2, 25 g of a solid, glass-like and slightly yellow-coloured product is obtained after decolourizing, extraction and evaporation.

An aqueous solution at 50% w/w has an absorbance at 470 nm of 0.1 ($E_{470}=0.2$).

EXAMPLE 6

500 g of glycol-ether (1) and 90 g of anhydrous glucose are charged to a flask of 1 liter of capacity equipped with stirrer, thermometer and distillation head.

The reaction mixture is heated at 119°–120° C. and then 3 g is added of a pyridine salt with a secondary alkyl sulfonic acid with an average chain length of 15 carbon atoms (briefly referred to as "SASA").

The catalyst was prepared as follows: 25 g of technical SASA, obtained by operating as disclosed in Italian Patent Application No. 20,878 A/89 to the name of Enichem Augusta S.p.A. and constituted by 68% of secondary alkyl sulfonic acid with average molecular weight $MW_{ave}$ 293, 8% of secondary alkyl disulfonic acid with $MW_{ave}$ 373, 8% of $H_2SO_4$, balance water, is treated with an excess of pyridine.

A syrup-like solution is obtained which is thoroughly dehydrated under reduced pressure at 100° C. in Rotavapor.

The residue is diluted with 100 cc of ethyl ether.

The resulting precipitate, constituted by pyridinium sulfate, is filtered off and the ethereal solution is concentrated again to dryness.

23 g is obtained of a slightly yellow paste which is used as such in the glucosidation reaction.

As soon as the catalyst is added, the reaction equipment is connected with a vacuum pump and the internal pressure inside the system is reduced down to 25 mmHg.

Water formed in the reaction is collected inside a trap cooled at $-80°$ C.

Heating under reduced pressure is continued for 6 hours, with 8.7 g of water being collected.

The reaction mixture is cooled, diluted with 500 cc of cold hexane and the insoluble matter is filtered off.

The precipitate, thoroughly washed with hexane and dried, yields 15.1 of a white, crystalline compound which, on HPLC (high-pressure liquid chromatography) analysis, is essentially. constituted by glucose and can hence be recycled.

The hexanic solution is admixed with 0.4 g of $CH_3ONa$ and is distilled under reduced pressure, first in Rotavapor at 30–40 mmHg and 50°–100° C. in order to recover hexane, and then under 0.1 mmHg and heating with an oil bath up to 190° C., in order to recover an excess of 423 g of glycol ether (1).

The distillation residue (143 g) is dissolved in 200 cc of $H_2O$ and is decolourized by treatment with $H_2O_2$ at 60°–70° C., with the pH value of the solution being kept at 8–9 by adding aqueous NaOH at 10% by weight/weight (w/w).

The aqueous solution is then extracted twice, each time with 300 cc of ethyl acetate and is subsequently concentrated to dryness.

127 g is obtained of a solid, glass-like, slightly yellow-coloured product which displays a similar composition to the product obtained in example 2.

EXAMPLE 7

To the same apparatus of Example 6, 500 g of glycol ether (1) and 90 g of anhydrous glucose are charged.

The reaction mixture is heated at 119°–120° C., and 1.5 g of Py.p-TSA are added.

As soon as the catalyst is added, the reaction equipment is connected with a vacuum pump and the internal pressure of the system is reduced down to 25 mmHg.

Water formed in the reaction is collected inside a trap cooled at $-80°$ C.

Heating under reduced pressure is continued for 6 hours; 9.0 g of water are collected.

Then, by subsequently operating as in Example 6, after dilution with hexane and filtering, 14.5 g of glucose are obtained.

From the hexanic phase, by distillation under reduced pressure, dilution with water, decolourization, extraction and drying, 126 g are obtained of a surfactant showing identical characteristics to those as of the product obtained from Example 2.

EXAMPLE 8

Comparison test with p-toluene sulfonic acid

The test is carried out as in Example 7, but using, as the catalyst, 1.02 of anhydrous p-toluene sulfonic acid (corresponding, as mol number, to 1.5 g of Py.p-TSA of Example 7).

The reaction mixture is heated at 119°–120° C. and under a pressure of 25 mmHg until the same amount of water as of Example 7 (9.0 g) is obtained.

The heating time is 2 hours and 45 minutes.

After heating, the reaction mixture, to the contrary to what was observed in Example 7, appears to be turbid owing to the presence of a solid phase constituted by extremely fine, difficultly settling particles.

Also the filtering operation, which in the test of Example 7 takes place within a few minutes, is very laborious owing to the effect of the very fine precipitate which tends to clog the fritted filter.

The white precipitate, thoroughly washed with hexane and dried, has a weight of 18.2 g and, differently to glucose obtained in Example 7, is not reduced by Fehling's reactant.

The HPLC analysis (high pressure liquid chromatography), using a $C_{18}$ Hypersil column and eluting with a gradient of from 100% to 0% of $H_2O=:CH_3CN$ and a Light Scattering detector, displays a wide peak corresponding to a retention time of approximately 16 minutes (glucose, under the same conditions, has a retention time of about 2,5 minutes).

To this compound a polyglucosidic structure can hence be attributed, and therefore it cannot be used again and recycled as, on the contrary, may be the case with glucose recovered in Example 7.

EXAMPLE 9

Opening of dodecene-alpha-epoxide with ethylene glycol 600 g of ethylene glycol are charged to a flask of 1 liter of capacity equipped with stirrer, thermometer and dipping tube for nitrogen flow.

1.5 g of sodium metal are added portionwise and the reaction mixture is stirred until dissolution is complete.

To the resulting solution, 200 cc of dodecene alpha-epoxide (purity 92%) are added and the mixture is heated at 110°–120° C. for 1 hour, with the disappearance of epoxide being monitored by thin-layer chromatography with eluent petroleum ether:ethyl ether=2:1.

The reaction product is distilled under reduced pressure, with the excess of ethylene glycol being recovered first and then the fraction being collected which distils at 160°–165° C./0.2 mmHg.

The latter is constituted by 210 g of product of formula (III), which solidifies at room temperature.

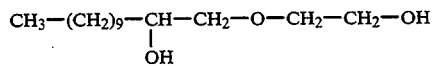
(3)

EXAMPLE 10

Reaction of (3) with glucose 100 g of product (3) and 18 g of glucose are charged to the same reaction equipment as of Example 2.

The reaction is heated at 120° C. and 0.3 g of Py.p-TSA is added.

The reaction equipment is connected with a vacuum pump, and the internal pressure is reduced down to 25 mmHg.

Heating at the same temperature is continued until a homogeneous, clear and slightly yellow coloured solution is obtained (about 45 minutes).

The reaction is neutralized with 70 mg of $CH_3ONa$ and is distilled under reduced pressure. 82.6 g of glycol ether (3) are recovered.

The residue, dissolved in 60 cc of water, decolourized and extracted as in Example 2 yields, after evaporating the aqueous solution, 32.1 g of a white solid product.

We claim:

1. A process for producing a hydroxyalkyl glucoside having the formula (I):

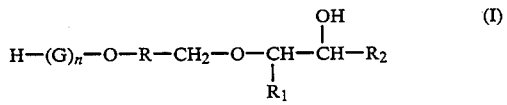

wherein:
(i) R is selected from the group consisting of —$CH_2$—, —$CH_2$—$CH_2$— and —$CH_2$—CHOH—;
(ii) each of $R_1$ and $R_2$ is an alkyl radical having 1–18 carbon atoms, or a hydrogen atom, with the proviso that $R_1$ and $R_2$ may not both be hydrogen atoms;
(iii) the combined total number of carbon atoms between $R_1$ and $R_2$ is not greater than 18;
(iv) G is a monosaccharide radical; and
(v) n is an integer from 1 to 5;
said process comprising:
(a) reacting an epoxide of an olefin having from 8 to 20 carbon atoms with a diol or a triol in the presence of a catalyst, so as to produce a glycol-ether; and
(b) glycosidating the glycol ether so produced with a reducing sugar, a compound which can supply a reducing sugar upon hydrolysis, or a methyl-, ethyl- or butyl-glucoside derivative of said reducing sugar, the glycosidating being carried out in the presence of a binary catalyst consisting of a strong organic acid and a weak organic base having a Ka value from $10^{-8}$ to $10^{-1}$.

2. The process of claim 1, wherein the strong organic acid of the binary catalyst used in step (b) is selected from the group consisting of: benzene- and alkylbenzene sulfonic acids, naphthalene and alkylnaphthalene sulfonic acids, primary, secondary and tertiary alkyl sulfonic acids, monoalkylsulfates, mono- and dialkylphosphates, and alkyl-, aryl- and alkylaryldisulfonic acids in which all aliphatic chains contain from 1 to 20 carbon atoms and sulfonic groups contain cation exchange resins.

3. The process of claim 1, wherein the weak organic base of the binary catalyst used in step (b) is selected from the group consisting of: pyridine, picolines, lutidines, collidines, quinoline, isoquinoline, quinaldine, pyriazine, pteridine, and tetramethylurea.

4. The process of claim 1, wherein the binary catalyst used in step (b) is selected from the group consisting of pyridine salts with alkylbenzene sulfonic acids or with secondary alkyl sulfonic acids.

5. The process of claim 1, wherein the binary catalyst used in step (b) is the salt of pyridine with secondary alkyl sulfonic acids (SASA) containing from 14 to 17 carbon atoms.

6. The process of claim 1, wherein the binary catalyst used in step (b) is prepared by mixing equivalent amounts of a strong organic acid and of a weak organic base having a Ka value from $10^{-8}$ to $10^{-1}$.

7. The process of claim 1, wherein the binary catalyst used in step (b) is used in an amount from 0.0001 to 0.1 mole per mole of reducing sugar or equivalent thereof.

8. The process of claim 7, wherein the binary catalyst used in step (b) is used in an amount from 0.01 to 0.05 mole per mole of reducing sugar or equivalent thereof.

9. The process of claim 1, wherein in step (b) the molar ratio of the reducing sugar or equivalent thereof to the glycol-ether is from 1:2 to 1:10.

10. The process of claim 9, wherein in step (b) the molar ratio of the reducing sugar or equivalent thereof to the glycol-ether is from 1:3 to 1:6.

11. The process of claim 1, wherein in step (b) the glycol-ether functions as a reaction solvent.

12. The process of claim 1, wherein the glycosidating is carried out at a temperature from 90° C. to 130° C.

13. The proccess of claim 12, wherein the glycosidating is carried out at a temperature from 110° C. to 120° C.

* * * * *